United States Patent [19]

Overmyer

[11] Patent Number: 5,785,523
[45] Date of Patent: Jul. 28, 1998

[54] DENTAL WATER LINE FLUSHING AND DISINFECTING SYSTEM

[76] Inventor: Thad J. Overmyer, 132 N. Second St., Danville, Ky. 40422

[21] Appl. No.: 911,620

[22] Filed: Aug. 15, 1997

[51] Int. Cl.⁶ .............................. A61C 19/00; A61L 2/00
[52] U.S. Cl. .................................................. 433/82; 422/28
[58] Field of Search ............................. 433/80, 82, 84, 433/104; 422/28

[56] References Cited

U.S. PATENT DOCUMENTS

| | | | |
|---|---|---|---|
| 3,481,689 | 12/1969 | Rosdahl et al. | 422/28 |
| 3,718,973 | 3/1973 | Slater et al. | 433/84 |
| 4,545,956 | 10/1985 | Ciszewski et al. | 422/28 |
| 4,668,190 | 5/1987 | Overmyer . | |
| 4,752,444 | 6/1988 | Bowen et al. | 422/28 |
| 4,990,087 | 2/1991 | De Rocchis et al. | 433/104 |
| 5,044,952 | 9/1991 | Castellini | 433/84 |
| 5,044,953 | 9/1991 | Sullivan | 433/92 |
| 5,295,829 | 3/1994 | Frey et al. | 433/82 |
| 5,308,579 | 5/1994 | Melon et al. | 422/28 |
| 5,318,443 | 6/1994 | Overmyer . | |
| 5,505,218 | 4/1996 | Steinhauser et al. | 134/95.1 |
| 5,526,841 | 6/1996 | Detsch et al. . | |
| 5,709,546 | 1/1998 | Waggoner | 433/82 |

FOREIGN PATENT DOCUMENTS

| | | | |
|---|---|---|---|
| 403 442 | 12/1990 | European Pat. Off. | 433/80 |
| 2270846 | 3/1994 | United Kingdom | 433/82 |

*Primary Examiner*—Ralph A. Lewis
*Attorney, Agent, or Firm*—Charles J. Brown

[57] ABSTRACT

In a dental unit which includes various devices, one being a dental handpiece, through which water and a lubricant-disinfectant solution passes, a water line flushing and disinfecting system wherein by an arrangement of double outlet and double inlet two-way valves pressurized air can expel all water and any loose material from the water lines and the devices, then pressurized air can expel the solution through the water lines and devices to disinfect them, and finally the solution can be expelled by the pressurized air through the water lines and devices.

5 Claims, 2 Drawing Sheets

DENTAL WATER LINE FLUSHING AND DISINFECTING SYSTEM

BACKGROUND OF THE INVENTION

With the increased awareness of the dangers of cross-infection from residual bacteria left in dental equipment after successive patient treatments, several advances have been made in the design and function of dental equipment to reduce contamination of as many equipment components as possible.

In my U.S. Pat. No. 5,318,443, I describe a method of flushing, disinfecting and lubricating a dental turbine handpiece by forcing a pressurized disinfectant solution and lubricant through an air drive line to the handpiece when it is not in operation to flush dental debris through an exhaust line. My U.S. Pat. No. 4,668,190 describes a system for injecting a solution, which could be a disinfectant into a dental water-injection system. The disinfectant solution within a reservoir is delivered by a separate port into the dental unit's water lines through a water reservoir or directly into the dental unit water line. U.S. Pat. No. 5,526,841 describes a decontamination system for water lines in dental units, in the form of a separate system which operates independently of the disinfecting of specific components such as dental handpieces as described in my U.S. Pat. No. 5,318,443.

It is the purpose of the present invention to provide a water line flushing and disinfecting system for a dental unit having various water-using devices including one or more which are supplied with their own disinfectant during use. More specifically it is an object of the present invention to improve upon single liquid-injection systems such as that described in my U.S. Pat. No. 4,668,190 so as to introduce disinfectant or flushing water not only through a dedicated line serving a particular device but also to any or all devices through which water passes in the dental unit. Water delivered to devices in a dental unit may stand in main or branch lines for periods long enough for bacteria film to form within the lines. Bacteria can also develop in water lines as a consequence of backflow of body fluids from patients through devices such as handpieces, syringes, scalers or basins. The system of the invention which permits in such water lines to be flushed and disinfected eliminates such bacteria growth and is designed to be integrated with existing systems for specific components of a dental unit.

SUMMARY OF THE INVENTION

In accordance with the invention a water line flushing and disinfecting system is provided for a dental unit. The dental unit has a plurality of devices, including a handpiece, through which devices water passes during operation, the water coming from a pressurized water source through various water lines. A pressurized disinfectant solution can be selectively delivered through a handpiece solution line along with or instead of water directly to the handpiece.

The water line flushing and disinfecting system of the invention includes a branch solution line extending from the handpiece solution line. A double outlet two-way valve is provided having a single inlet to which the branch solution line is connected. One of the two outlets of this double outlet valve is connected during normal operation of the dental unit to a solution feed line leading to the respective devices. A double inlet two-way valve is also provided. The first of its inlets is connected to the other of the two outlets of the double outlet two-way valve, and the second of its inlets is connected to a pressurized air source. This double inlet two-way valve has a single outlet connected to the water source. With these components, the water lines can be flushed and disinfected in a three step process. First, delivery of the solution to the devices is ceased, including delivery from the double outlet valve through the solution feed line. Second, air is released from the pressurized air source through the double inlet valve to expel all water from the water source through the water lines and out of the respective devices. Third, after ceasing such air flow releasing pressurized solution is released from the double outlet valve through the double inlet valve and the water source and water lines and out of the respective devices. The disinfectant solution is preferably left in the dental unit overnight. Before reuse of the dental unit air is again released from the pressurized air source through the double inlet valve to expel all remaining solution from the water lines and out of the respective devices.

In one form of the invention the water source is a water bottle pressurized by the pressurized air source. In another form of the invention the water source is a lateral line from a pressurized water main, with a check valve in the lateral line preventing backflow into the water main and with an on-off valve in the lateral line for ceasing delivery of water during the second and third steps of releasing pressurized air and then solution from the double outlet valve.

The preferred disinfectant solution includes glycerine, alcohol and chlorhexidine gluconate. In one form of the system an on-off valve is located in the solution feed line leading from the double outlet valve to the respective devices.

DESCRIPTION OF PREFERRED EMBODIMENT

Figure 1:
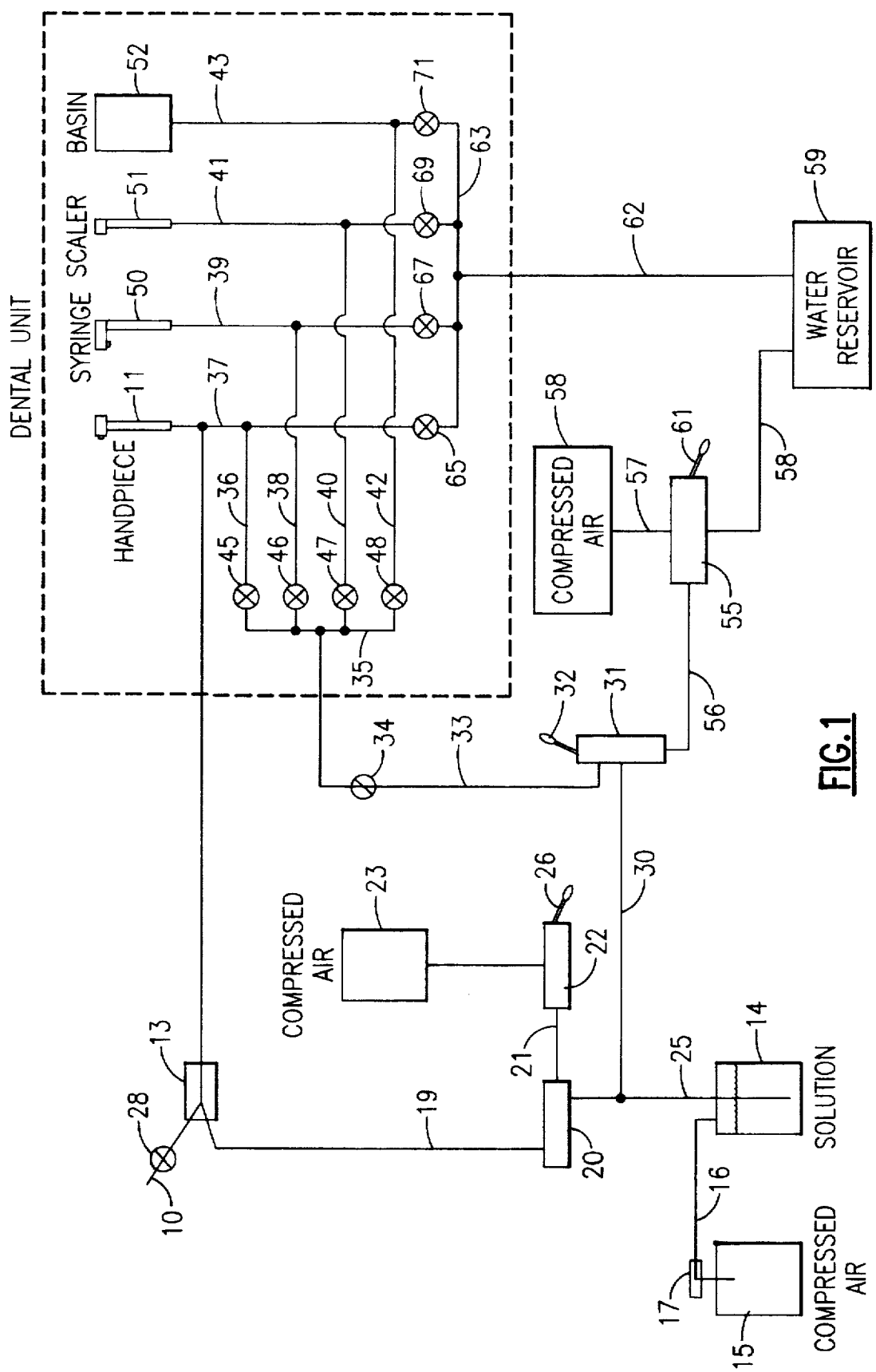
FIG. 1 is an overall schematic diagram of the system of the invention wherein the water source is a water bottle or reservoir.

Referring first to FIG. 1, it is to be understood that the system of the present invention includes as a component the liquid admixing means described in my U.S. Pat. No. 4,668,109 and particularly with reference to the FIG. 5 embodiment thereof. This known component of the system includes a water conduit 10 connected, through a handpiece feed line described hereinafter, to a high speed handpiece 11 through a low pressure venturi tube 13. During a drilling procedure water is injected into the patient's mouth through the handpiece 11.

A liquid additive reservoir 14 provides a source of additive liquid such as a disinfecting and lubricating solution comprising glycerine, alcohol and chlorhexidine gluconate. My U.S. Pat. No. 4,695,255 discloses further details of that solution. Alternatively, a less costly solution functioning only as a disinfectant may be used. An example is aqueous liquid bleach (NaOCl), perhaps 1500 to 5000 PPM in water, plus a surfactant and an anti-corrosive agent. If such an additive liquid is used the flushing and disinfecting system described herein would be operated only two or three times a week and the solution would be left in the dental unit for only about fifteen minutes rather than overnight.

Pressurized air is delivered to the ullage space over the solution in the reservoir 14 from a compressed air source 15 through an air line 16. A pressure regulator 17 is provided in the airline 16 to control the pressure level on the solution in the reservoir 14.

A first section of a handpiece solution line 19 is connected to the water conduit 10 by a Y-fitting having an approximately thirty degree included angle. To control solution flow, a valve 20 operated by a pneumatic pressure line 21 is manually operable by pneumatic means 22 connected to a compressed air source 23, all as described in my U.S. Pat. No. 4,668,190. A second section 25 of the handpiece solution line extends from the valve 20 downwardly into the reservoir 14 to receive flow of the solution from the lower level of the reservoir 14 when pressurized air through the air line 16 increases the air pressure in the ullage space above the solution. All of the foregoing is fully described in my U.S. Pat. No. 4,668,170.

It will be understood that disinfectant solution from the solution reservoir 14 can be selectively introduced to admix with water in the venturi 13 by operation of a lever 26 on the pneumatic means 22 which allows more or less air from the compressed air source 23 to enter the valve 20. This mixture of water and disinfectant solution is thereby carried by the line 10 to and through the handpiece 11. An on-off valve 28 is provided in the line 10 so that disinfectant solution alone can be carried to the handpiece 11 if desired.

The components of the water line flushing and disinfecting system of the invention integrated with the foregoing known components will now be described. A branch disinfectant solution line 30 extends from the section 25 of the handpiece solution line. The branch solution line 30 is connected to a single inlet of a conventional double outlet two-way valve 31 having an operating lever 32. One outlet of the two-way valve 31 is connected during normal operation of the dental unit to a solution feed line 33 leading through an on-off valve 34 to a manifold 35 in the dental unit. From the manifold 35 respective feed lines extend to the various devices in the dental unit which utilize water. Thus a subline 36 extends to a handpiece feed line 37 to which the line 10 also connects, a subline 38 extends to a syringe feed line 39, a subline 40 extends to a scaler feed line 41 and a subline 42 extends to a basin feed line 43. The sublines 36, 38, 40 and 42 are provided with respective on-off valves 45, 46, 57 and 48. A syringe 50 is provided at the operating end of the syringe feed line 39, a scaler 51 is provided at the operating end of the scaler feed line 41, and a basin 52 is provided at the operating end of the basin feed line 43.

In the normal function of the dental unit the operating lever 32 on the double outlet two-way valve 31 is in a position directing the disinfectant solution from the reservoir 14 through the solution feed lines 30 and 33 to the on-off valve 34. When the on-off valve 34 is open the disinfectant solution proceeds through the manifold 35 to those of the sublines 36, 38, 40 and 42 which are selected to be opened by suitable operation of the valves 45, 56, 47 and 48. By this arrangement the solution may be directed from the branch line 30 to any or all of the handpiece 11, syringe 50, scaler 51 or basin 52 as may be desired.

A double inlet two-way valve 55 is provided with one of its inlets 56 being the second outlet of the double outlet two-way valve 31. Another inlet 57 into the double inlet two-way valve 55 leads from a pressurized air source 58. The compressed air sources 15, 23 and 58 may in actual practice be a single source.

The double inlet two-way valve 55 has a single outlet 58 extending to a water source, which in the embodiment of FIG. 1 is a water reservoir 59. An operating lever 61 on the double inlet two-way valve 55 permits it to direct either compressed air from the source 58 or disinfectant solution through the line 56, through the outlet 58 and through the water reservoir 59.

A line 62 extends from the water reservoir 59 to the dental unit where it divides in a manifold 63 into the handpiece feed line 37, the syringe feed line 39, the scaler feed line 41 and the basin feed line 43. Selected flow from the manifold 63 into these feed lines is achieved by operation of respective on-off valves 65, 67, 69 and 71.

In the operation of the system of FIG. 1, the water lines can be flushed and disinfected by first closing the valve 20 by operation of the lever 26 so as to cease flow of disinfectant solution to the handpiece 11 through the line 10 and 37. At the same time the valve 34 is closed to cease flow through the line 33 to one or more of the handpiece 11, syringe 50, scaler 51 and basin 52. Then the double inlet two-way valve 55 is operated by the lever 61 to cease solution flow through the inlet 56 and allow compressed air to pass from the source 58 through the inlet 55 and single outlet 58 to expel all water from the reservoir 59 and through the line 62 and its various sublines to and through the devices 11, 50, 51 and 52 in the dental unit. When only air emerges from the devices 11, 50, 51 and 52 all water throughout the water lines has been expelled.

Next the levers 32 and 61 on the double outlet two-way valve 31 and the double inlet two-way valve 55 are operated to release pressurized disinfectant solution from the reservoir 14 through the branch line 30 and the two-way valves 31 and 55 into the reservoir 59 and thence through the lines 62 and its sublines. When the disinfectant solution emerges from the handpiece 11, the syringe 50, the scaler 51 and the basin 52, the disinfecting step has been completed. The lever 32 is operated to cease solution flow through the line 56. At this point the solution may be left in the dental unit lines overnight or for ten to fifteen minutes if the additive liquid is only a disinfectant. In any case, after that period the bottle which functioned as the reservoir 14 can be filled with fresh water and utilized as a reservoir 59 and the reservoir 59 containing the remaining disinfectant solution may be used as the reservoir 14 for the next cycle of operation. In that next cycle, the lever 61 is operated to briefly direct compressed air from the source 58 and then through the water reservoir 59 and the water lines to expel the remaining disinfectant solution. The levers 26, 32 and 61 are then operated to return the system to its starting condition where disinfectant solution can be mixed with air in the line 10 or through the line 33 to one or more of the devices 11, 50, 51 and 52, and water is forced from the water reservoir 59 through one or more of the devices 11, 50, 51 and 52.

Figure 2:
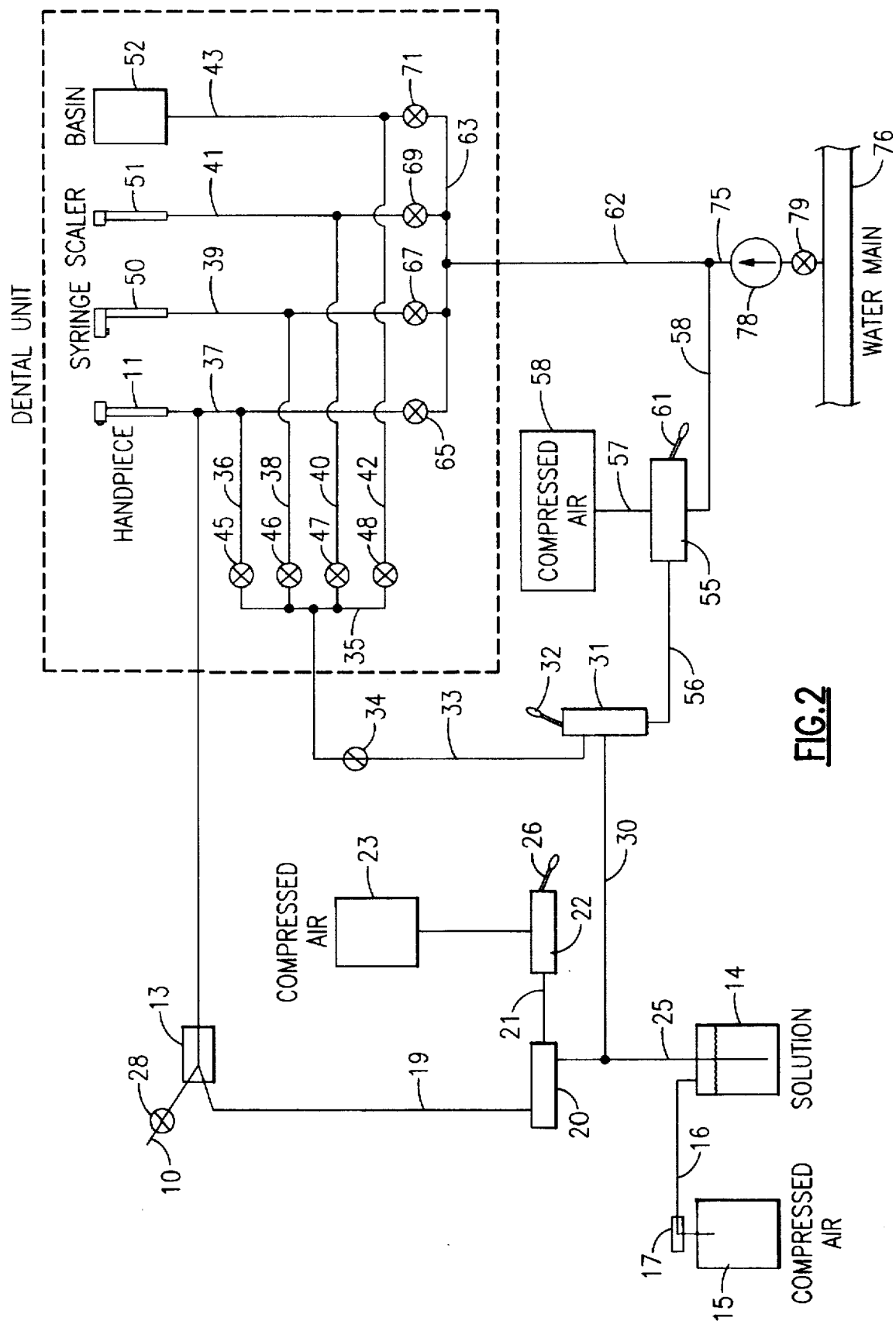
FIG. 2 is a similar diagram of the overall system wherein the water source is a lateral line from a pressurized water main.

FIG. 2 illustrates another embodiment of the system of the invention where the water source is not a water reservoir but instead is a lateral line 75 extending from a water main 76. A check valve 78 is provided in the lateral line 75 to prevent back flow into the water main 76 and an on-off valve 79 may be included to cease the supply of water to the dental unit if desired. All other components of the embodiment of FIG. 2 are the same as in the embodiment of FIG. 1 and are therefore similarly numbered. The operation of the system of FIG. 2 is virtually the same as that of FIG. 1 except that when disinfectant solution or compressed air is directed through the line 58 it proceeds directly through the line 62 without passing through any other components such as the water reservoir 59 in FIG. 1. In the step of flushing the disinfectant solution through the dental unit with water, the valve 79 is simply opened to emit pressurized water from the water main 76 without reliance upon the pressurized air source 58 as in the embodiment of FIG. 1. No switching of disinfectant and water reservoirs is involved in the operation of the FIG. 2 embodiment.

The scope of the invention is to be determined by the following claims rather than from the foregoing description of preferred embodiments.

I claim:

1. In combination with a dental unit having a plurality of devices, including a handpiece, through which devices water passes during operation, the water coming from a pressurized water source through water lines, and wherein a pressurized disinfectant solution can be selectively delivered through a handpiece solution line directly to the handpiece through its water line, a water line flushing and disinfecting system comprising a) a branch solution line extending from the handpiece solution line;
   b) a double outlet two-way valve having a single inlet to which said branch solution line is connected and having one of its two outlets connected during normal operation of the dental unit to a solution feed line leading to the respective devices; and
   c) a double inlet two-way valve having one of its inlets connected to the other of the two outlets of the double outlet two-way valve and the other of its inlets connected to a pressurized air source and having a single outlet connected to said water source;
   d) whereby the water lines can be flushed and disinfected by first ceasing delivery of the solution to the devices, including delivery from said double outlet valve through the solution feed line, second releasing air from the pressurized air source through the double inlet valve to expel all water from the water source through the water lines and out of the respective devices, third after ceasing such air flow releasing pressurized solution from the double outlet valve through the double inlet valve and the water source and the water lines and out of the respective devices, and finally releasing air from the pressurized air source through the double inlet valve to expel all remaining solution from the water lines and out the respective devices.

2. A water line flushing and disinfecting system according to claim 1 wherein the water source is a water bottle pressurized by said pressurized air source.

3. A water line flushing and disinfecting system according to claim 1 wherein the water source is a lateral line from a pressurized water main, a check valve being located in the lateral line for preventing backflow into said water main, and an on-off valve being located in the lateral line for ceasing delivery of water during the second and third steps of releasing pressurized air and then solution from the double outlet valve.

4. A water line flushing and disinfecting system according to claim 1 wherein the solution comprises glycerin, alcohol and chlorhexidine gluconate.

5. A water line flushing and disinfecting system according to claim 1 wherein an on-off valve is located in the solution feed line leading from the double outlet valve to the respective devices.

* * * * *